(12) United States Patent
Leukel et al.

(10) Patent No.: US 6,555,103 B2
(45) Date of Patent: Apr. 29, 2003

(54) BIOMEDICAL MOLDINGS

(75) Inventors: Jörg Leukel, Freiburg (DE); Peter Chabrecek, Riehen (CH); Dieter Lohmann, Münchenstein (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/929,670

(22) Filed: Aug. 14, 2001

(65) Prior Publication Data

US 2002/0022013 A1 Feb. 21, 2002

(30) Foreign Application Priority Data

Aug. 14, 2000 (DE) .......................... 001 17 520

(51) Int. Cl.$^7$ .............................. A61K 31/74
(52) U.S. Cl. ................................. 424/78.04
(58) Field of Search .................. 424/78.04, 427; 623/5; 514/764

(56) References Cited

U.S. PATENT DOCUMENTS 5,713,957 A * 2/1998 Steele et al. ............. 623/5.16
6,468,667 B1 * 10/2002 Chabrecek et al. ......... 428/532

FOREIGN PATENT DOCUMENTS

| WO | WO 95/13764 | * | 5/1995 |
| WO | WO 99/08717 | * | 2/1999 |

* cited by examiner

*Primary Examiner*—Jose G. Dees
*Assistant Examiner*—Konata M. George
(74) *Attorney, Agent, or Firm*—Robert J. Gorman, Jr.; R. Scott Meece; Richard I. Gearhart

(57) ABSTRACT

The present invention is concerned with a biomedical molding comprising a non-biodegradable biocompatible organic polymer comprising attached to its surface radicals of formula

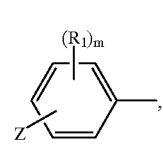

(1)

wherein the variables are as defined in the claims. The biomedical moldings of the invention are radiation sensitive and may be used, for example, as intraocular lens in ophthalmic surgery.

12 Claims, No Drawings

BIOMEDICAL MOLDINGS

The present invention pertains to moldings, especially biomedical moldings such as ophthalmic moldings, comprising certain radiation sensitive groups on their surface and to a process for attaching said moldings to living tissue, in particular to the eye as a corneal prosthesis.

It is known e.g. from WO 95/13764 to provide corneal prostheses being composed of porous polymeric material for correcting the optical properties of an eye or altering the appearance thereof. Corneal inlays are in general implanted into or onto the cornea of a mammal using surgical methods, for example by making an incision in the stromal tissue of the cornea to form a pocket into which the onlay is placed, and then closing the incision by suturing.

A more recent method involves removing the corneal epithelial cell layers of the cornea by scraping, placing a synthetic lenticule directly onto and in intimate contact with the corneal tissue and holding it in place for a period of time which is sufficient for the epithelial cells to recover, grow over the implant and thus fix it in a persistent manner. The initial temporary fixation of the onlay on the cornea is accomplished by the use of a biocompatible glue such as a commercially available collagen- or fibrin-based two components glue. However said glues have not yet proven satisfactory mainly because of severe handling problems. For example, the surgeon always has to mix the glue components prior to use. Once the premixing has taken place, only a limited time period is available for using the glue depending on the glue's specific curing time; this puts time-pressure on the surgeon. Following the attachment of the onlay onto the cornea, excessive glue has to be removed carefully because otherwise cured glue residues may inhibit the overgrowth of epithelial cells over the onlay. Further disadvantages of the known glues concern, for example, an insufficient mechanical stability and duration. In view of these and other drawbacks, there is a need for improved methods and materials for a temporary fixation of a polymeric onlay on a cornea.

Surprisingly, it now has been found that biomedical moldings, in particular ophthalmic moldings such as corneal onlays, may be attached conveniently to living tissue if they comprise certain radiation sensitive groups covalently bound to their surface.

The present invention therefore in one aspect pertains to a biomedical molding comprising a non-biodegradable biocompatible organic polymer comprising attached to its surface radicals of formula

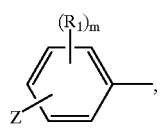

(1)

wherein $R_1$ is, for example, hydroxy, $C_1$–$C_4$-alkyl, $C_1$–$C_4$-alkoxy, sulfo, nitro, trifluoromethyl or halogen such as, for example, fluorine or chlorine, m is an integer from 0 to 2, and Z is a group which functions as a triggerable precursor for carbene, nitrene or benzhydrol formation.

Examples of suitable biocompatible organic polymers to which the radicals of formula (1) are attached are polyaddition and polycondensation polymers, for example polyurethanes, epoxy resins, polyethers, polyesters, polyamides or polyimides; polyolefins, for example polyacrylates, polymethacrylates, polystyrene, polyethylene or halogenated derivatives thereof, polyvinyl acetate or polyacrylonitrile; or elastomers, for example silicones, polybutadiene or polyisoprene.

A preferred group of organic polymers are those being conventionally used for the manufacture of biomedical devices, e.g. ophthalmic devices such as contact lenses, artificial cornea ot intraocular lenses, which are not hydrophilic per se. Such materials are known to the skilled artisan and may comprise for example polysiloxanes, perfluoroalkyl polyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, polyolefines, or fluorinated polyolefines, such as polyvinylidene fluoride, fluorinated ethylene propylene, or tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene. A group of particularly preferred hydrophobic polymers are non-porous or particularly porous perfluoroalkyl polyether (PFPE) homo- or copolymers or perfluoroalkyl acrylates or methacrylates, for example those as disclosed in PCT applications WO 96/31546, WO 96/31548, WO 97/35906 or WO 00/15686.

Another preferred group of biocompatible organic polymers are those being conventionally used for the manufacture of biomedical devices, e.g. contact lenses, which are hydrophilic per se, since hydrophilic groups, e.g. carboxy, carbamoyl, sulfate, sulfonate, phosphate, amine, ammonium or hydroxy groups, are inherently present in the material. Such materials are known to the skilled artisan and comprise for example polyhydroxyethyl acrylate, polyhydroxyethyl methacrylate (HEMA), polyvinyl pyrrolidone (PVP), polyacrylic acid, polymethacrylic acid, polyacrylamide, poly-N,N-dimethyl acrylamide (DMA), polyvinyl alcohol, copolymers for example from two or more monomers from the group hydroxyethyl acrylate, hydroxyethyl methacrylate, N-vinyl pyrrolidone, acrylic acid, methacrylic acid, acrylamide, N,N-dimethyl acrylamide, vinyl alcohol, vinyl acetate and the like, polyalkylene glycols such as polyethylene glycols, polypropylene glycols or polyethylene/polypropylene glycol block copolymers. Typical examples are e.g. Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon or Atlafilcon.

Another group of preferred organic polymers are amphiphilic segmented copolymers comprising at least one hydrophobic segment and at least one hydrophilic segment which are linked through a direct bond or a bridge member. Examples are silicone hydrogels, for example those disclosed in PCT applications WO 96/31792 and WO 97/49740.

The form of the organic polymer may vary within wide limits. Examples are moldings of all kinds, for example tubes, films, membranes and in particular ophthalmic moldings, such as contact lenses, intraocular lenses or artificial cornea. Further examples of moldings are materials useful for example as wound healing dressings, eye bandages, materials for the sustained release of an active compound such as a drug delivery patch, moldings that can be used in surgery, such as heart valves, vascular grafts, catheters, artificial organs, encapsulated biologic implants, e.g. pancreatic islets, materials for prostheses such as bone substitutes, or moldings for diagnostics, membranes or biomedical instruments or apparatus.

Z in formula (1) is, for example, a group of formula

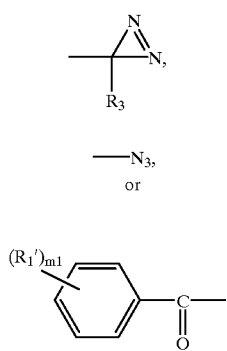

(2a)

(2b)

(2c)

wherein $R_3$ is an electron-withdrawing substituent, for example, fluorinated $C_1$–$C_6$-alkyl, such as a radical —$C_2F_5$ or preferably a radical —$CF_3$, $R_1'$ independently has the meaning of $R_1$, and m1 independently has the meaning of m.

$R_1$ and $R_1'$ are each independently of the other preferably $C_1$–$C_4$-alkoxy, $C_1$–$C_4$-alkyl or sulfo.

The variable m is 1 or preferably 0. The variable m1 is preferably 0.

One group of suitable radicals of formula (1) are those wherein Z is a group

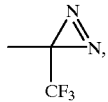

and m is 0.

A further group of suitable radicals of formula (1) are those wherein Z is a group —$N_3$, and m is 1 or preferably 0.

The radicals of formula (1) may be attached to the molding surface by any known linking group that is biomedically acceptable and especially ophthalmically acceptable. For example, the radicals of formula (1) may be attached directly to the molding surface by means of a functional group, for example by a functional group of formula —C(O)—X— (3a) or —X₁—C(O)— (3b); or —X₁—C(O)—X— (3c); or —X₁—C(S)—X— (3d);

wherein X and X₁ are each independently of the other a group —O— or —NR₂—, wherein R₂ is hydrogen or $C_1$–$C_4$-alkyl. X and X₁ are each independently preferably a group —O— or —NH— and in particular a group —NH— each.

A preferred direct linking group between the radical of formula (1) and the molding surface is of formula (3a), (3b) or (3c). The radicals of formulae (3a)-(3d) are in each case to be understood that the left bond is directed to the radical of formula (1), and the right bond is directed to the organic polymer surface.

A preferred embodiment of the invention thus relates to a biomedical molding comprising attached to its surface radicals of the formula

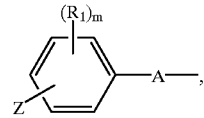

(1a)

wherein $R_1$, m and Z are as defined above, and A is a radical of the formula (3a), (3b), (3c) or (3d) above. Preferably, Z is a group of formula

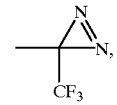

m is 0, and A is a radical of formula (3a) above. In another preferred embodiment, Z is a group —$N_3$, m is 1 or preferably 0 and A is a radical of formula (3b) or (3d), in particular (3b).

Biomedical moldings comprising attached to their surface radicals of the formula (1a) may be prepared, for example, by reacting a compound of formula

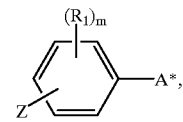

(1')

wherein A* is a radical —$X_1$H, —NCO, —NCS, —COOH or a carboxy derivative, for example an acid halide, optionally activated ester, or anhydride, and $R_1$, Z, $X_1$ and m are as defined above, with a coreactive group of the molding surface, which may be, for example, a radical —XH, —NCO, —NCS, —COOH or a carboxy derivative, for example an acid halide, ester or anhydride.

For example, the reactions of a compound of formula (1') having a carboxy, carboxylic acid halide group, preferably activated ester, acid anhydride, lactone, isocyanato or isothiocyanato group with an amino or hydroxy compound of the molding surface, or vice versa, are well-known in the art and may be carried out as described in textbooks of organic chemistry. For example, the reaction of an isocyanato or isothiocyanato derivative of formula (1') with an amino- or hydroxy-compound of the molding surface may be carried out in an inert organic solvent such as an optionally halogenated hydrocarbon, for example petroleum ether, methylcyclohexane, toluene, chloroform, methylene chloride and the like, or an ether, for example diethyl ether, tetrahydrofurane, dioxane, or a more polar solvent such as DMSO, DMA, N-methylpyrrolidone or even a lower alcohol, at a temperature of from 0 to 100° C., preferably from 0 to 50° C. and particularly preferably at room temperature, optionally in the presence of a catalyst, for example a tertiary amine such as triethylamine or tri-n-butylamine, 1,4-diazabicyclooctane, or a tin compound such as dibutyltin dilaurate or tin dioctanoate. It is advantageous to carry out the above reactions under an inert atmosphere, for example under an nitrogen or argon atmosphere.

In case of a compound of formula (1') or the molding surface carrying a carboxy anhydride group, the reaction of the carboxy anhydride with the molding surface or the compound of formula (1') carrying an amino or hydroxy group may be carried out as described in organic textbooks, for example in an aprotic solvent, for example one of the above-mentioned aprotic solvents, at a temperature from room temperature to about 100° C.

In case of a compound of formula (1') or the molding surface carrying a carboxy group, the reaction of the carboxy group with the molding surface or the compound of formula (1') carrying an amino or hydroxy group may be carried out under the conditions that are customary for ester or amide formation, for example in an aprotic medium at a temperature from about room temperature to about 100° C. It is further preferred to carry out the esterification or amidation reaction in the presence of an activating agent, for example N-ethyl-N'-(3-dimethylaminopropyl)carbodiimide (EDC), N-hydroxy succinimide (NHS), sulfo-N-hydroxy succinimide or N,N'-dicyclohexyl carbodiimide (DCC) or in the presence of an o-(benztriazole)-uronium salt such as o-(benztriazol-1-y-)-N,N,N,N-tetramethyluronium hexafluorophosphate. Most preferably, the carboxylic acid derivative of formula (1') is previously converted to an activated ester using one of the above-mentioned activating agents, and the activated ester is then further reacted with the hydroxy or preferably amino groups of the surface.

The resulting modified biomedical moldings are advantageously purified before use, for example by washing or extraction in a suitable solvent.

The compounds of formula (1') are known and partly commercially available or may be prepared according to known processes.

Suitable coreactive functional groups may be inherently (a priori) present at the molding surface to be modified. If the molding surface contains too few or no reactive groups, the material surface can be modified previously by methods known per se, for example plasma chemical methods (see, for example, WO 94/06485), or conventional functionalization with groups such as —OH, —NH$_2$ or —CO$_2$H produced.

Preferably, amino or hydroxy groups of the molding surface are reacted with a compound of formula (1') having a coreactive carboxy, carboxylic acid anhydride, activated carboxylic acid ester, carboxylic acid halide, isocyanate or isothiocyanate group. According to an also preferred alternative, carboxy, activated carboxylic acid ester or carboxylic acid halide groups of the surface are reacted with a compound of formula (1') having a coreactive amino or hydroxy group.

According to a further embodiment of the invention, the radicals of formula (1) are attached to the molding surface by means of a spacer group. Suitable spacer groups are, for example, of formula

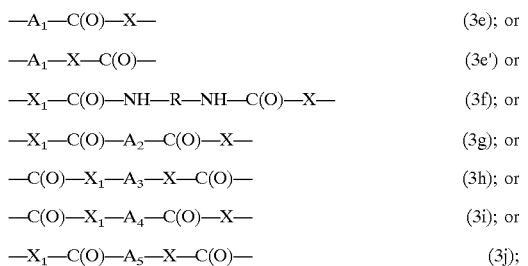

wherein A$_1$ is C$_1$–C$_{30}$-alkylene which may be interrupted by —O— except for C$_1$-alkyl;

A$_2$ is C$_1$–C$_{200}$-alkylene which may be interrupted by —O— except for C$_1$-alkyl;

A$_3$ is C$_2$–C$_{200}$-alkylene which may be interrupted by —O or —NH—;

A$_4$ and A$_5$ are each independently C$_2$–C$_{200}$-alkylene which may be interrupted by —O—, —NH—, —C(O)NH—, —NH(CO)—, —C(O)O— or —O(O)C—;

R is linear or branched C$_1$–C$_{18}$-alkylene or unsubstituted or C$_1$–C$_4$-alkyl- or C$_1$–C$_4$-alkoxy-substituted C$_6$–C$_{10}$-arylene, C$_7$–C$_{18}$-aralkylene, C$_6$–C$_{10}$-arylene-C$_1$–C$_2$-alkylene-C$_6$–C$_{10}$-arylene, C$_3$–C$_8$-cycloalkylene, C$_3$–C$_8$-cycloalkylene-C$_1$–C$_6$-alkylene, C$_3$–C$_8$-cycloalkylene-C$_1$–C$_2$-alkylene-C$_3$–C$_8$-cycloalkylene or C$_1$–C$_6$-alkylene-C$_3$–C$_8$-cycloalkylene-C$_1$–C$_6$-alkylene; and X and X$_1$ are as defined above.

The radicals of formulae (3e)–(3j) are in each case to be understood that the left bond is directed to the radical of formula (1) and the right bond is directed to the organic polymer surface.

A$_1$ is preferably a branched or preferably linear C$_1$–C$_{12}$-alkylene radical or a radical —(CH$_2$CH$_2$O)$_{1\text{-}5}$—CH$_2$CH$_2$— and in particular linear C$_1$–C$_4$-alkyl or —(CH$_2$CH$_2$O)$_{1\text{-}3}$—CH$_2$CH$_2$—.

R as alkylene in formula (3f) is preferably a linear or branched C$_3$–C$_{14}$alkylene radical, more preferably a linear or branched C$_4$–C$_{12}$alkylene radical and most preferably a linear or branched C$_6$–C$_{10}$alkylene radical.

When R is arylene, it is, for example, naphthylene or especially phenylene, each of which may be substituted, for example, by C$_1$–C$_4$-alkyl or by C$_1$–C$_4$-alkoxy. Preferably, R as arylene is 1,3- or 1,4-phenylene that is unsubstituted or substituted by C$_1$–C$_4$-alkyl or by C$_1$–C$_4$-alkoxy in the ortho-position to at least one linkage site.

R as aralkylene is preferably naphthylalkylene and most preferably phenylalkylene. The alkylene group in aralkylene contains preferably from 1 to 12, more preferably from 1 to 6 and most preferably from 1 to 4 carbon atoms. Most preferably, the alkylene group in aralkylene is methylene or ethylene.

When R is cycloalkylene, it is preferably C$_5$–C$_6$cycloalkylene and most preferably cyclo-hexylene that is unsubstituted or substituted by methyl.

When R is cycloalkylene-alkylene, it is preferably cyclopentylene-C$_1$–C$_4$-alkylene and especially cyclohexylene-C$_1$–C$_4$-alkylene, each unsubstituted or mono- or poly-substituted by C$_1$–C$_4$-alkyl, especially methyl. More preferably, the group cycloalkylene-alkylene is cyclohexylene-ethylene and, most preferably, cyclohexylene-methylene, each unsubstituted or substituted in the cyclohexylene radical by from 1 to 3 methyl groups.

When R is alkylene-cycloalkylene-alkylene, it is preferably C$_1$–C$_4$-alkylene-cyclopentylene-C$_1$–C$_4$-alkylene and especially C$_1$–C$_4$-alkylene-cyclohexylene-C$_1$–C$_4$-alkylene, each unsubstituted or mono- or poly-substituted by C$_1$–C$_4$-alkyl, especially methyl. More preferably, the group alkylene-cycloalkylene-alkylene is ethylene-cyclohexylene-ethylene and, most preferably, is methylene-cyclohexylene-methylene, each unsubstituted or substituted in the cyclohexylene radical by from 1 to 3 methyl groups.

R as C$_3$–C$_8$-cycloalkylene-C$_1$–C$_2$-alkylene-C$_3$–C$_8$-cycloalkylene or C$_6$–C$_{10}$-arylene-C$_1$–C$_2$-alkylene-C$_6$–C$_{10}$-arylene is preferably C$_5$–C$_6$-cycloalkylene-methylene-C$_5$–C$_6$-cycloalkylene or phenylene-methylene-phenylene, each of which may be unsubstituted or substituted in the cycloalkyl or phenyl ring by one or more methyl groups.

The radical R in formula (3f) has a symmetrical or, preferably, an asymmetrical structure.

A preferred group of spacer radicals comprises those of formula (3f), wherein R is linear or branched $C_6$–$C_{10}$alkylene; or cyclohexylene-methylene or cyclohexylene-methylene-cyclohexylene each unsubstituted or substituted in the cyclohexyl moiety by from 1 to 3 methyl groups.

The bivalent radical R in formula (3f) is derived preferably from a diisocyanate and most preferably from a diisocyanate selected from the group isophorone diisocyanate (IPDI), 4,4'-methylenebis(cyclohexyl isocyanate), 1,6-diisocyanato-2,2,4-trimethyl-n-hexane (TMDI), methylenebis(cyclohexyl-4-isocyanate) and hexamethylene diisocyanate (HMDI).

$A_2$ in formula (3g) is preferably linear or branched $C_1$–$C_{24}$-alkylene or $C_4$–$C_{160}$-alkylene which is interrupted by —O—, more preferably $C_1$–$C_6$-alkylene or $C_8$–$C_{60}$-alkyl which is interrupted by —O— and most preferably $C_1$–$C_4$-alkylene or -(alk)-O—$(CH_2CH_2O)_{8-25}$-(alk)-, wherein (alk) is, for example, $C_1$–$C_6$-alkyl, preferably $C_1$–$C_4$-alkyl, more preferably $C_1$–$C_3$-alkyl and in particular ethyl.

$A_3$ is preferably linear or branched $C_1$–$C_{24}$-alkylene or $C_4$–$C_{160}$-alkylene which is interrupted by —O— or —NH—, more preferably $C_1$–$C_6$-alkylene or $C_8$–$C_{60}$-alkyl which is interrupted by —O—, and most preferably $C_1$–$C_4$-alkylene, or a radical -(alk)-O—$(CH_2CH_2O)_{8-25}$-(alk)-, wherein (alk is as defined above.

$A_4$ as alkylene is, for example, branched or preferably linear $C_2$–$C_{24}$-alkylene, more preferably $C_2$–$C_{18}$-alkylene and in particular $C_4$–$C_{12}$-alkylene. An alkylene radical $A_4$ which is interrupted by —O— is, for example, a radical —$(CH_2CHR_5O)_x$-(alk)-, wherein (alk) is as defined above, $R_5$ is hydrogen or methyl and x is from about 2 to about 99. A preferred alkylene radical $A_4$ which is interrupted by —O— is a radical —$(CH_2CH_2O)_x$—$(CH_2CH_2)$—, wherein x is from 4 to 80 and in particular from 8 to 80. An alkylene radical $A_4$ which is interrupted by —C(O)NH— is, for example, a polypeptide radical of formula —$(CHR_6$—C(O)NH)_t$—$CHR_6$—, wherein $R_6$ is hydrogen or $C_1$–$C_4$alkyl which is unsubstituted or substituted by hydroxy, carboxy, carbamoyl, amino, phenyl, o-, m- or p-hydroxyphenyl, imidazolyl, indolyl or a radical —NH—C(=NH)—$NH_2$ and t is an integer from about 2 to 80. An alkylene radical $A_4$ which is interrupted by —C(O)O— or —OC(O)— is, for example, a polyester radical. A preferred radical of formula (3i) corresponds to formula —C(O)O—$(CH_2CH_2O)_{8-80}$—$CH_2CH_2$—C(O)NH— or —C(O)O-(alk')-C(O)NH— wherein (alk') is branched or preferably linear $C_2$–$C_{18}$-alkylene.

$A_5$ as alkylene is, for example, branched or preferably linear $C_2$–$C_{24}$-alkylene, more preferably $C_2$–$C_{18}$-alkylene and in particular $C_4$–$C_{12}$-alkylene. An alkylene radical $A_5$ which is interrupted by —O— is, for example, a radical -(alk)-$(OCHR_4CH_2)_x$—, wherein (alk) is as defined above, $R_4$ is hydrogen or methyl and x is from about 2 to about 99. A preferred alkylene radical $A_5$ which is interrupted by —O— is a radical —$(CH_2CH_2)$—$(OCH_2CH_2)_x$—, wherein x is from 4 to 80 and in particular from 8 to 80. An alkylene radical $A_5$ which is interrupted by —NHC(O)— is, for example, a polypeptide radical of formula —$CHR_5$—(NHC(O)—$CHR_5)_t$—, wherein $R_5$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—$NH_2$ and t is an integer from about 2 to 80. An alkylene radical $A_5$ which is interrupted by —C(O)O— or —OC(O)— is, for example, a polyester radical.

A further preferred embodiment of the invention thus relates to a biomedical molding comprising attached to their surface radicals of the formula

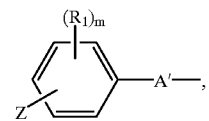

(1b)

wherein for $R_1$, m and Z each the above given meanings and preferences apply, and A' is a radical of the formula (3e), (3e'), (3f), (3g), (3h), (3i) or (3j) above and preferably a radical of formula (3f), (3g) or (3i), wherein for the variables contained therein the above mentioned meanings and preferences apply.

Biomedical moldings comprising attached to their surface radicals of formula (1b) wherein A'is a radical of formula (3e) above may be prepared, for example, by reacting a compound of formula

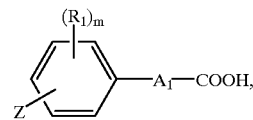

(1")

wherein $A_1$, $R_1$, Z and m are as defined above, or a carboxy derivative thereof, for example a halide, ester or anhydride thereof, with —XH groups of the molding surface, wherein X is as defined above. Moldings comprising attached to their surface radicals of formula (1b) wherein A' is a radical of formula (3e') above may be prepared, for example, by reacting a compound of formula (1') above, wherein A* is a radical —$X_1H$, with carboxy groups or a derivative thereof of the molding surface.

Biomedical moldings comprising attached to their surface radicals of formula (1b) wherein A' is a radical of formula (3f) or (3g) above may be prepared, for example, by reacting a compound of formula (1') above, wherein A* is a radical —$X_1H$, and —XH groups of the molding surface, wherein X and $X_1$ are as defined above, in any order with a compound of formula ONC—R—NCO wherein R is as defined above, or with a compound of formula HOOC—$A_3$—COOH or an above mentioned carboxy derivative thereof, wherein $A_3$ is as defined above.

Biomedical moldings comprising attached to their surface radicals of formula (1b) wherein A' is a radical of formula (3h) above may be prepared, for example, by reacting a compound of formula (1') above, wherein A* is a radical —COOH or an above mentioned carboxy derivative thereof, and —COOH groups or an above mentioned carboxy derivative thereof of the molding surface, in any order with a compound of formula $X_1H$—$A_3$—XH wherein X and $X_1$ are as defined above.

Biomedical moldings comprising attached to their surface radicals of formula (1b) wherein A' is a radical of formula (3i) above may be prepared, for example, by reacting a compound of formula (1') above, wherein A* is a radical —COOH or an above mentioned carboxy derivative thereof, and —XH groups of the molding surface, in any order with a compound of formula $HX_1$—$A_4$—COOH or an above mentioned carboxy derivative thereof, wherein $A_4$, X and $X_1$, are as defined above.

Biomedical moldings comprising attached to their surface radicals of formula (1b) wherein A' is a radical of formula (3i) above may be prepared, for example, by reacting a compound of formula (1') above, wherein A* is a radical —X₁H, and —COOH groups or an above mentioned carboxy derivative thereof of the molding surface, in any order with a compound of formula HOOC—A₅—XH wherein A₅, X and X₁, are as defined above.

The compounds of formula (1') and (1") as well as the compounds of formulae ONC—R—NCO, HOOC—A₃—COOH, X₁H—A₃—XH, HX₁—A₄—COOH and HOOC—A₅—XH are well known in the art and commercially available in part. In addition, the reactions between reactive groups of the molding surface, a suitable compound of formula (1') or (1") and optionally one of the above mentioned bifunctional compounds to yield a moldings surface comprising radicals of the formula (1b) may be carried out in each case under conditions that are customary for ester, amide, urethane or urea formation, for example as outlined above.

Throughout the application terms such as carboxy, carboxylic acid, —COOH, sulfo, —SO₃H, amino, —NH₂ and the like always include the free acid or amine as well as a suitable salt thereof, for example a biomedically or in particular occularly acceptable salt thereof such as, for example, a sodium, potassium, ammonium salt or the like (of an acid), or a hydrohalide such a hydrochloride (of an amine).

According to still another embodiment of the invention, the radiation sensitive radicals of formula (1) may be attached to the biomedical molding by a process comprising the steps of (i) providing the molding surface with reactive groups by a plasma induced polymerization of an ethylenically unsaturated compound carrying a reactive group; and (ii) reacting the reactive groups of the modified molding surface with a coreactive compound comprising a radical of formula (1). A suitable process for the plasma induced polymerization of functional monomers is described, for example, in WO 98/28026. Suitable functional monomers which may be used in this step are any polymerizable unsaturated compound which carries reactive groups and can be evaporated and introduced into a plasma generating apparatus to contact the material to be coated provided therein. Examples of reactive groups to be contemplated herein include isocyanate (—NCO), isothiocyanate (—NCS), epoxy, anhydride, azlactone and lactone (e.g. β-, γ-, δ-lactone) groups. A suitable vinyl monomer having a reactive group in this context is, for example, a compound of formula

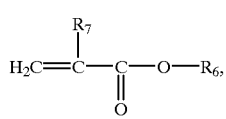

(4a)

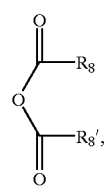

(4b)

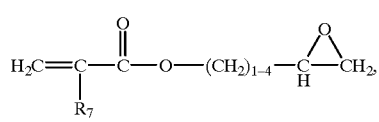

(4c)

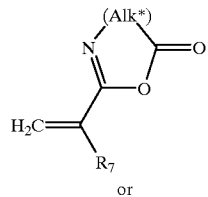

(4d)

or

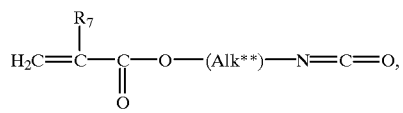

(4e)

wherein R₆ is hydrogen, unsubstituted or hydroxy-substituted C₁–C₆-alkyl or phenyl,
R₇ is hydrogen, C₁–C₄-alkyl or halogen,
R₈ and R₈' are each an ethylenically unsaturated radical having from 2 to 6 C-atoms, or R₈ and R₈' together form a bivalent radical —C(R₇)=C(R₇')— wherein R₇ is as defined above and
R₇' independently has the meaning of R₇, and
(Alk*) is C₁–C₆-alkylene, and (Alk**) is C₂–C₁₂-alkylene.

The following preferences apply to the variables contained in formulae (4a)-(4e):
R₆ is preferably hydrogen or hydroxy-C₁–C₄-alkyl, in particular hydrogen or β-hydroxyethyl.
R₇ is preferably hydrogen or methyl.
R₈ and R₈' are preferably each vinyl or 1-methylvinyl, or R₈ and R₈' together form a radical —C(R₇)=C(R₇')— wherein R₇ and R₇' are each independently hydrogen or methyl.
(Alk*) is preferably methylene, ethylene or 1,1-dimethyl-methylene, in particular a radical —CH₂— or —C(CH₃)₂—.
(Alk**) is preferably C₂–C₄-alkylene and in particular 1,2-ethylene.

Particularly preferred vinyl monomers having a reactive group are 2-isocyanatoethylmethacrylate (IEM), 2-vinyl-azlactone, 2-vinyl-4,4-dimethyl-azlactone, acrylic acid, methacrylic acid, acrylic anhydride, maleic acid anhydride, 2-hydroxyethylacrylate (HEA), 2-hydroxymethacrylate (HEMA), glycidylacrylate or glycidylmethacrylat.

Suitable coreactive compounds in step (ii) comprising a radical of formula (1) are, for example, of formula (1') above, wherein A* is, for example, —X₁H, —COOH or a carboxy derivative, for example an acid halide, ester or anhydride thereof, and R₁, Z and m are as defined above.

Biomedical moldings according to the invention that comprise radicals of the formula (1) are radiation sensitive, that is to say upon irradiation, for example with UV or visible light, the molding surface is provided with highly reactive carbene, nitrene or benzhydrol radicals which may react with all kinds of organic material including synthetic and natural polymers with the formation of covalent —C—C— or —C—N—C— bonds. Accordingly, the biomedical moldings of the invention may be attached chemically on virtually every organic material including living tissue which turn them into a valuable tool for surgery, particularly for ophthalmic surgery.

It is thus a particular object of the invention to provide a corneal onlay, comprising attached to its surface radicals of the formula (1). Said onlay may be composed of any of the known synthetic materials with the requisite mechanical properties, as mentioned above. The corneal onlay is adapted for epithelial recolonization, which means, that the polymeric material from which the onlay is formed does not inhibit cellular attachment or motility. The radicals of formula (1) are attached to the synthetic material making up the onlay as described above. According to one embodiment of the invention, only a part of the onlay, preferably the inner anterior surface only, is provided with radicals of formula (1) in order to fix it on the cornea. According to another embodiment, both the outer posterior and anterior surface of the onlay, are provided with radicals of formula (1). The provision of the posterior surface of the onlay with radiation sensitive radicals may serve to further modify the outer onlay surface, for example in order to facilitate cellular attachment as is hereinafter described.

The fixation of an corneal onlay according to the present invention on the cornea may be initiated, for example, by irradiation, particularly by irradiation with UV or visible light. Preferably, the cornea is previously prepared for the attachment of the onlay, for example by removing the epithelial cell layers of the cornea by scraping. In general, the onlay is placed in intimate contact with the corneal tissue and is then irradiated. Suitable light sources for the irradiation are known to the artisan and comprise for example mercury lamps, high pressure mercury lamps, xenon lamps, carbon arc lamps or sunlight. Sensitizers may be used to shift the irradiation wavelength. In addition, a suitable filter may be used to limit the irradiation to a specific wavelength range. Preferably, the onlay surface to which have been previously applied the compound(s) comprising radicals of formula (1) is irradiated with light of a wavelength $\geq 300$ nm, preferably from 350 to 400 nm. The time period of irradiation is not critical but is usually in the range of up to 30 minutes, preferably from 10 secondes to 10 minutes, and more preferably from 15 seconds to 5 minutes, and particularly preferably from 20 seconds to 1 minute.

One preferred method of implanting a corneal onlay onto a cornea thus comprises
(i) providing an onlay comprising groups of formula (1) at its anterior surface only;
(ii) placing the onlay in contact with the corneal tissue; and
(iii) irradiating the onlay whereby the onlay is fixed on the cornea.

Subsequent to the above fixation of the onlay on the cornea, the posterior surface of the implant may be coated with a tissue growth promoting compound as described hereinafter.

Another preferred method of implanting a corneal onlay onto a cornea comprises
(i) providing an onlay comprising groups of formula (1) at both its posterior and anterior surface,
(ii) placing the onlay in contact with the corneal tissue;
(iii) before or after step (ii) coating the posterior surface with one or more components which promote the growth of tissue adjacent to the implanted onlay, and
(iv) irradiating the onlay whereby the onlay is fixed on the cornea, and the tissue growth promoting compound is fixed on the posterior onlay surface.

Suitable tissue growth promoting compounds in both above mentioned methods are, for example, albumine, extracellular matrix (ECM), fibronectin, laminin, chondroitan sulfate, collagen, cell-attachment proteins, anti-gelatine factor, cold-insoluble globulin, chondronectin, epidermal growth factor, mussel adhesive protein, sialo proteins, thrombospondin, vitronectin, and various proteoglycans, and/or derivatives of the above or mixtures thereof. Preferred tissue growth promoting compounds are collagen, cell-attachment proteins or epidermal growth factor.

The biomedical moldings of the invention provide a new route towards implanting a corneal onlay onto a cornea which is easy to perform, does not affect the wearers vision, and is safe. In particular, a mechanical stable fixation of the implant on the cornea is obtained which lasts for a period of time sufficient for the epithelial cells to recover, grow over the implant and thus fix it in a persistant manner. The onlays are very easy to handle, since the use thereof does not involve, for example, a premixing of glue components or time pressure of the surgeon due to specific curing times of the glue components. In addition, no tedious removal of excess glue after fixing the onlay onto the cornea is necessary, and the previous problem of inhibition of overgrowth by glue residues does not exist. Moreover, the onlays of the invention may be stored conveniently for a long time, for example in form of a patch with cover foils protecting the surface(s). The onlay is then immediately ready for use, by just removing the cover foil(s) from the surface(s). All of the advantages mentioned above naturally apply not only to contact lenses but also to other biomedical moldings according to the invention as mentioned before.

In the examples, if not indicated otherwise, amounts are amounts by weight, temperatures are given in degrees Celsius.

EXAMPLE 1

Synthesis of a Diazirine NHS Ester 7.06 g (36.81 mmol) N-ethyl-N'-(3-dimethylaminopropyl)carbodiimide hydrochloride are given into a 500 mL round bottom flask filled with 200 mL water at pH 12. After 15 minutes stirring at room temperature 50 mL dichlormethane are added. The extraction is repeated three times with 50 mL dichlormethane. The organic phases are combined, dried over $MgSO_4$, filtered and dried at high vacuum. The free base is given into a 250 mL round bottom flask and dissolved in 150 mL acetonitrile (28.4 ppm water). 17.19 g (~12 mmol Cl) Merrifield polymer is added. The suspension is heated to 100° C. under reflux for 16 hours. After cooling to room temperature the activated Merrifield polymer is washed 3 times with 50 mL acetonitrile, 2 times with 50 mL diethylether and dried at high vacuum. 300 mg (1.30 mmol) 4-(1-azi-2,2,2-trifluoroethyl)benzoic acid, 135 mg (1.17 mmol) N-hydroxysuccinimide, 6.3 g activated Merrifield polymer and 45 mL chloroform are given into a 100 mL brown round bottom flask and shaked at room temperature. DC control indicates complete conversion after 30 minutes. The mixture is filtered and washed with chloroform. The filtrate is dried at high vacuum. Complete reaction is determined by 1 H-NMR spectroscopy.

EXAMPLE 2

Amino Functionalization of Lenticules Using 1,2-Diaminocyclohexane Plasma DACH

Lenticules composed of a perfluoroalkyl polyether material (synthesis see WO 00/15686, Example 2) are, after extraction in isopropanol, toluene and again in isopropanol, placed on the glass holder within the plasma reactor equipped with an external ring electrode and a 27.13 MHz radiofrequency (RF) generator for the generation of an inductively-coupled, cold glow discharge plasma. The distance between the substrates and the lower edge of the plasma zone is 12 cm. The reactor is evacuated to a pressure of 0.008 mbar, and held at these conditions for one hour. Then, the argon plasma gas flow rate into the plasma zone of the reactor is set to 20 sccm (standard cubic centimeter), the pressure in the reactor is adjusted to 0.12 mbar and the RF generator is switched on. The plasma discharge of a power 250 Watts is maintained for a total period of 1 min (in order to clean and activate the lenses surfaces). Afterward the 1,2-DACH vapor is introduced into the reactor chamber from DACH reservoir (maintained at 24° C.) at 0.15 mbar for 1 min. After this, the following parameters for the plasma polymerization of DACH are chosen: Argon flow rate for plasma excitation=5 sccm, Argon carrier gas flow rate for DACH transport=5 sccm, temperature of the DACH evaporation unit=24° C., the distance between the lower edge of the plasma zone and the substrates=5 cm, pressure=0.2 mbar, and plasma power=100 W. The lenticules are treated for about 5 minutes with a pulsing glow discharge plasma (1 μsec. on, 3 μsec. off). After 5 minutes of deposition the plasma discharge is interrupted and DACH vapor is let to flow into reactor for other 5 min. The reactor is then evacuated and maintained for 30 minutes at a pressure 0.008 mbar in order to remove residual monomer and activated spices. The internal pressure is brought to atmospheric by using dry nitrogen.

A portion of the lenticules having been treated on the inner anterior surface is unloaded from the reactor. Another portion of lenticules is kept in the reactor, turned over and the whole procedure is repeated to coat the other side of the substrates.

EXAMPLE 3

Binding of a Photo-Reactive Diazirine onto Lenticules Without Spacer 9.25 mg of the diazirine NHS ester of Example 1 are dissolved in 12 mL isopropanole. 8 lenticules from Example 2 having DACH plasma on one side (amino density 12/nm$^2$) are pitched between two metal grids, added to the solution and moderately shaken for 72 hours at room temperature. The lenticules are extracted 4 times with 12 mL isopropanole and equilibrated stepwise to water.

EXAMPLE 4

Binding of a Photo-Reactive Diazirine onto Lenticules via a Hydrophilic Spacer

The NHS ester of a bifunctional polyethylenglycol (PEG) of formula

HOOC—(CH$_2$CH$_2$O)$_x$—CH$_2$CH$_2$—FMOC wherein FMOC is 9-fluorenylmethylcarbamate and the average of x is about 75 to 80 (molecular weight 3400 Da, Shearwater) is prepared according to the method as described in Example 1.

84.3 mg of the FMOC-PEG-NHS ester (28 μmol,) are dissolved in 7 mL acetonitrile. 7 lenticules of Example 2 (DACH plasma on one side, amino density 12/nm$^2$) are added and shaken overnight at room temperature. The lenticules are extracted 10 times with 7 mL acetonitrile. The solvent is removed and 7 mL of 20% piperidine in acetonitrile are added and shaken for 30 minutes. An extraction with 7 times 7 mL acetonitrile is performed. The solvent is exchanged to isopropanole. 19.8 mg of Example A are dissolved in 7 mL isopropanole and added to the lenticules and shaken at room temperature overnight. The lenticules are extracted 7 times with 7 mL isopropanole. After extraction the lenticules are equilibrated to water.

EXAMPLE 5

Binding of a Photo-Reactive Diazirine onto Lenticules via a Hydrophobic Spacer 1 g amino undecan acid (4.9 mmol) and 100 mL water are mixed. To the suspension 6 mL 1n HCl (6 mmol) are added. The clear solution is freezing dried. The acid group of amino undecan acid hydrochloride is transferred to the NHS active ester using the method of Example 1. 60 mg of the NHS ester undecan amino hydrochlorid are dissolved in 3 mL acetonitrile. 3 mL isopropanole are added. 7 lenticules of Example 2 (DACH plasma on one side, amino density 12/nm$^2$) are added and shaken for 72 hours. The lenticules are extracted with isopropanole and acetonitrile. 6 droplets of triethylamine are added and shaken for 4 hours. The lenticules are extracted 5 times with 7 mL acetonitrile. The solution is changed to isopropanole. After the addition of 20.1 mg of the compound of Example 1 the whole is shaken overnight. The lenticules are then extracted 6 times with 7 mL isopropanole and finally equilibrated to water.

EXAMPLE 6

Testing of Adhesive Strength on Sample Pig Eyes

Epithelium of fresh pig eyes is removed. Photo-reactive lenticules of Example 3, 4 and 5 are put from an aqueous solution and the water is removed from the lenticules surface using a wipe. The lenticules are given onto the pig eyes by softly pressing. A blue light source (EFOS lamp) is used for irradiation. After irradiation for 120 seconds some droplets of water are given onto the lenticules. The glue testing is performed by 3 methods: finger push test, peel-off test and a stability test putting the glued lenticules with pig eye in saline for several days. All samples are compared to those without irradiation. High adhesive properties are found for Example 3 and very high for Example 5. High adhesive properties are found for Example 4.

EXAMPLE 7

Glue Testing on Eye of Living Cats

The Epithelium of the cat eye is removed and the lenticule of Example 3 is put onto eye as described in Example 6. After irradiation for 120 seconds using a blue light lamp the cat is observed for glue stability. The lenticule stays in the cat eye for 2 days, and healthy looking epithelial cells have protruded over the rim of the onlay and have started to cover it. After removal of the lenticule the cells grow over the wound completely.

What is claimed is:

1. A biomedical molding comprising a non-biodegradable biocompatible organic polymer comprising attached to its surface radicals of formula (1)

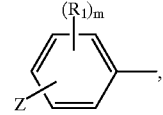

wherein R$_1$ is hydroxy, C$_1$–C$_4$-alkyl, C$_1$–C$_4$-alkoxy, sulfo, nitro, trifluoromethyl or halogen, m is an integer from 0 to 2, and Z is a group which functions as a triggerable precursor for carbene, nitrene or benzhydrol formation.

2. A biomedical molding according to claim 1, wherein the biocompatible organic polymer is selected from a polyurethane, epoxy resin, polyether, polyester, polyamide, polyimide, polyolefine, polybutadiene, polyisoprene and a silicone.

3. A biomedical molding according to claim 1, wherein the biocompatible organic polymer is selected from a polysiloxane, perfluoroalkyl polyether, fluorinated poly(meth)acrylate, polyalkyl (meth)acrylate, polyolefine and a fluorinated polyolefine.

4. A biomedical molding according to claim 1, wherein Z in formula (1) is a group of formula

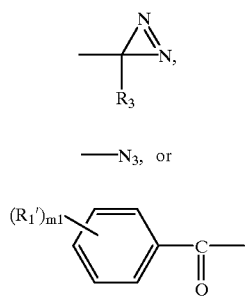

wherein $R_3$ is fluorinated $C_1$–$C_6$-alkyl, $R_1'$ is hydroxy, $C_1$–$C_4$-alkyl, $C_1$–$C_4$-alkoxy, sulfo, nitro, trifluoromethyl or halogen, and m1 is 0 or 1.

5. A biomedical molding according to claim 1, comprising attached to its surface radicals of formula

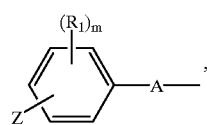

wherein $R_1$, m and Z are defined as in claim 1, and A is a functional group of formula

wherein X and $X_1$ are each independently of the other a group —O— or —$NR_2$—, and $R_2$ is hydrogen or $C_1$–$C_4$-alkyl.

6. A biomedical molding according to claim 1, comprising attached to its surface radicals of formula

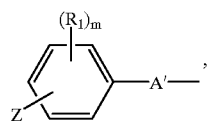

wherein $R_1$, m and Z are each as defined in claim 1, and A' is a spacer group of formula

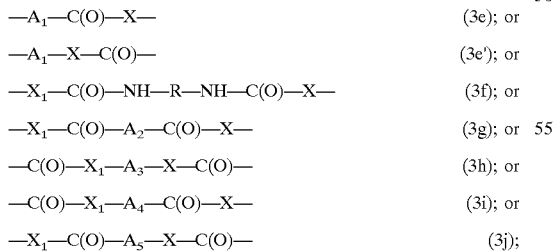

wherein
- $A_1$ is $C_1$–$C_{30}$-alkylene which may be interrupted by —O—;
- $A_2$ is $C_1$–$C_{200}$-alkylene which may be interrupted by —O— except for $C_1$-alkyl;
- $A_3$ is $C_2$–$C_{200}$-alkylene which may be interrupted by —O— or —NH—;
- $A_4$ and $A_5$ are each independently $C_2$–$C_{200}$-alkylene which may be interrupted by —O—, —NH—, —C(O)NH—, —NH(CO)—, —C(O)O— or —O(O)C—;
- R is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene; X and $X_1$ are each independently of the other a group —O— or —$NR_2$—, and $R_2$ is hydrogen or $C_1$–$C_4$-alkyl.

7. A biomedical molding according to claim 1, wherein the radicals of formula (1) are attached to the molding surface by a process comprising the steps of
(i) providing the molding surface with reactive groups by a plasma induced polymerization of an ethylenically unsaturated compound carrying a reactive group; and
(ii) reacting the reactive groups of the modified molding surface with a coreactive compound comprising a radical of formula (1).

8. A biomedical molding according to claim 1, which is a corneal onlay.

9. A process for implanting a corneal onlay onto a cornea comprising the steps of
(i) providing an onlay comprising groups of formula (1) according to claim 1 at its anterior surface only;
(ii) placing the onlay in contact with the corneal tissue; and
(iii) irradiating the onlay whereby the onlay is fixed on the cornea.

10. A process for implanting a corneal onlay onto a cornea comprising the steps of
(i) providing an onlay comprising groups of formula (1) according to claim 1 at both its posterior and anterior surface,
(ii) placing the onlay in contact with the corneal tissue,
(iii) before or after step (ii) coating the posterior surface with one or more components which promote the growth of tissue adjacent to the implanted onlay; and
(iv) irradiating the onlay whereby the onlay is fixed on the cornea, and the tissue growth promoting compound is fixed on the posterior onlay surface.

11. A process according to claim 10, wherein the tissue growth promoting compound is an albumine, extracellular matrix (ECM), fibronectin, laminin, chondroitan sulfate, collagen, cell-attachment protein, anti-gelatine factor, cold-insoluble globulin, chondronectin, epidermal growth factor, mussel adhesive protein, sialo protein, thrombospondin, vitronectin, proteoglycan, or a mixture of two or more of the compounds mentioned.

12. A method of using a non-biodegradable biocompatible organic polymer comprising attached to its surface radicals of formula

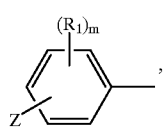

wherein
$R_1$ is an electron-withdrawing substituent, m is an integer from 0 to 2, and
Z is a group which functions as a triggerable precursor for carbene, nitrene or benzhydrol formation, as an intraocular lens for the implantation into or onto a cornea, comprising the step of attaching said organic polymer to the cornea.

* * * * *